(12) United States Patent
Lavielle et al.

(10) Patent No.: US 6,326,377 B1
(45) Date of Patent: Dec. 4, 2001

(54) SUBSTITUTED HYDROCHROMENOPYRIDINES

(75) Inventors: Gilbert Lavielle, La Celle Saint Cloud; Thierry Dubuffet, Chevilly-la-Rue; Patrick Hautefaye, Servon Brie Comte Robert; Françoise Lejeune, Saint Cloud; Mark Millan, Le Pecq, all of (FR)

(73) Assignee: Adir et Compagnie, Courbevoie (FR)

( * ) Notice: Subject to any disclaimer, the term of this patent is extended or adjusted under 35 U.S.C. 154(b) by 0 days.

(21) Appl. No.: 09/480,037

(22) Filed: Jan. 10, 2000

Related U.S. Application Data

(62) Division of application No. 09/103,304, filed on Jun. 23, 1998, now Pat. No. 6,090,837.

(30) Foreign Application Priority Data

Jun. 24, 1997 (FR) .................................. 97 07839

(51) Int. Cl.⁷ .................... A61K 31/44; A61K 31/40; A61P 25/00; C07D 491/12; C07D 401/00
(52) U.S. Cl. .................. 514/291; 514/338; 514/411; 546/89; 546/276.7; 548/430
(58) Field of Search ................. 514/291; 546/89

(56) References Cited

U.S. PATENT DOCUMENTS 6,080,752 * 6/2000 Stemp et al. .......................... 514/290

OTHER PUBLICATIONS

J. Med. Chem., 1989, 32, 720–727.

\* cited by examiner

*Primary Examiner*—Brenda Coleman

(74) *Attorney, Agent, or Firm*—The Firm of Hueschen and Sage; G. Patrick Sage

(57) ABSTRACT

Compounds of formula (I):

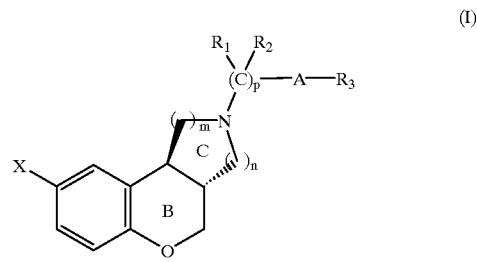

wherein:

m is 0 to 3 inclusive, n is 0 to 3 and $2 \leq m+n \leq 3$, p is 1 to 6 inclusive, X represents cyano or —CO—NR$_4$R$_5$, R$_4$ and R$_5$ being selected from hydrogen, linear or branched (C$_1$–C$_6$)-alkyl, (C$_3$–C$_7$)-cycloalkyl, and aryl, R$_1$ and R$_2$ each independently represent hydrogen or linear or branched (C$_1$–C$_6$)-alkyl, R$_3$ represents hydrogen, optionally substituted phenyl, naphthyl or heteroaryl, or aryloxy or arylthio, or aryl or heteroaryl substituted by A'—Cy, A' and Cy being as defined in the description, and medicinal products containing the same which are useful as D$_3$ receptor ligands.

9 Claims, No Drawings

SUBSTITUTED HYDROCHROMENOPYRIDINES

The present application is a division of our prior-filed application Ser. No. 09/103,304, filed Jun. 23, 1998, now U.S. Pat. No. 6,090,837.

The present invention relates substituted hydrochromenopyridines.

Apart from the fact that the compounds of the present invention are new, they have particularly valuable properties, binding selectively to $D_3$ receptors compared with $D_2$ receptors.

BACKGROUND OF THE INVENTION

The discovery of those $D_3$ dopaminergic receptors (P. Sokoloff et al., Nature, 1990, 347, 147), their strong concentration in the limbic system and their low density in lactotrophic cells and in the nigrostriated system, makes them a choice target for obtaining antipsychotics that do not have effects on the secretion of prolactin and are less liable to cause extrapyramidal-type syndromes. It has, in fact, been established that the dopaminergic pathways extending to the limbic system and the cortex play a decisive role in the control of mood and in the aetiology and treatment of psychiatric disorders such as schizophrenia, depression, anxiety, aggression and other impulsive disorders (M. J. Millan et al., Drug News & Perspectives, 1992, 5, 397–406; A. Y. Deutch et al., Schizophrenia, 1991, 4, 121–156; H. Y. Meltzen et al., Pharmacol. Rev., 1991, 43, 587–604).

DESCRIPTION OF THE PRIOR ART

The compounds of the prior art closest to those forming the subject of this Application were described for their dopaminergic or serotoninergic properties (EP 691342 J. Med. Chem., 1989, 32, 720–7).

The compounds of the present application are characterised by the presence of carboxamide or nitrile-type electron-attracting substituents which, surprisingly, allow enhancement of the $D_3$ dopaminergic properties in terms of strength and selectivity.

The selectivity makes the products of the invention especially valuable for use as medicaments acting on the dopaminergic system that do not have the undesirable effects of $D_2$ ligands. In the light of results that have appeared in the literature, it is possible for them to be used in the treatment of impulsive disorders (for example those caused by drug abuse, B. Caine, Science, 1993, 260, 1814), aggressiveness (J. W. Tidey, Behavioral Pharm., 1992, 3, 553), Parkinson's disease (J. Carlson, Neur. Transm., 1993, 94, 11), psychoses, memory disorders (P. Sokoloff et al., Nature, 1990, 347, 147), anxiety and depression (P. Willner, Clinical Neuropharm., 1985, 18, suppl. 1, 549–56).

DETAILED DESCRIPTION OF THE INVENTION

The present invention relates more specifically to compounds of formula (I):

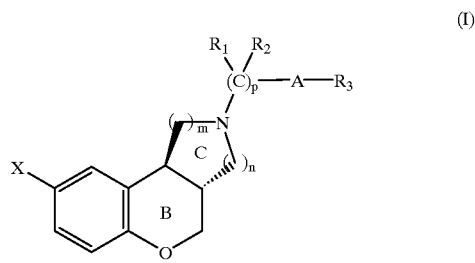

wherein:
m is an integer such that $0 \leq m \leq 3$,
n is an integer such that $0 \leq n \leq 3$ and $2 \leq m+n \leq 3$,
p is an integer such that $1 \leq p \leq 6$,
the junction between the B and C rings is in the trans configuration,
X represents a cyano group or a group —CO—NR$_4$R$_5$, R$_4$ and R$_5$ being selected from hydrogen, linear or branched (C$_1$–C$_6$)-alkyl, (C$_3$–C$_7$)-cycloalkyl and optionally substituted aryl,
A represents a a bond or a group selected from —NR—CO—, —CO—NR—, —NR—SO$_2$ and —SO$_2$—NR wherein R represents a hydrogen atom or a linear or branched (C$_1$–C$_6$)-alkyl group,
R$_1$ and R$_2$ each independently represent a hydrogen atom or a linear or branched (C$_1$–C$_6$)-alkyl group,
R$_3$ represents:
  a hydrogen atom, or a phenyl, naphthyl or heteroaryl group each of which is optionally substituted by one or more halogen atoms, linear or branched (C$_1$–C$_6$)-alkyl, linear or branched (C$_1$–C$_6$)-alkoxy, hydroxy, cyano, amino, nitro, carboxy, linear or branched (C$_1$–C$_6$)-perhaloalkyl, sulpho, acylamino, linear or branched (C$_1$–C$_6$)-alkylsulphonyl or linear or branched (C$_1$–C$_6$)-alkylsulphonylamino groups,
  an aryl or heteroaryl group substituted by a group A'—Cy wherein A' represents a σ bond, a linear or branched (C$_1$–C$_6$)-alkylene group (in which a carbon atom may optionally be replaced by an oxygen or sulphur atom), a linear or branched (C$_1$–C$_6$)-alkenylene group (in which a carbon atom may optionally be replaced by an oxygen or sulphur atom) or a group —NR—CO—, —CO—NR, —NR—SO$_2$— or SO$_2$—NR (in which R represents a hydrogen atom or a linear or branched (C$_1$–C$_6$)-alkyl group), and Cy represents an optionally substituted aryl group or an optionally substituted heteroaryl group,
  a 2-indolinon-5-yl group,
  or an aryloxy or arylthio group (with the proviso that in that case A represents a σ bond),
provided that:
  when n is 0, m is other than 2,
  when n is 1, R$_1$ and R$_2$ represent a hydrogen atom, A represents a σ bond and p is 1, R$_3$ is other than phenyl or pyridyl,
  when n is 1, R$_1$ and R$_2$ represent a hydrogen atom and A represents a σ bond, R$_3$ is other than a hydrogen atom,
  when n is 1, R$_1$ and R$_2$ represent a hydrogen atom and A represents an —NH—CO— group, R$_3$ is other than a hydrogen atom or a phenyl, naphthyl, or heterocyclic group selected from thienyl, furyl, pyrrolyl and pyridyl, each of those groups being optionally substituted by one or more halogen atoms or trihalomethyl, alkoxy or hydroxy groups, their isomers, enantiomers and diastereoisomers, and also the addition salts thereof with a pharmaceutically acceptable acid or base.

Among the pharmaceutically acceptable acids there may be mentioned by way of non-limiting example hydrochloric, hydrobromic, sulphuric, acetic, trifluoroacetic, lactic, malonic, succinic, glutamic, fumaric, maleic, citric, oxalic, methanesulphonic, benzenesulphonic and camphoric acid etc.

Among the pharmaceutically acceptable bases there may be mentioned by way of non-limiting example sodium hydroxide, potassium hydroxide, triethylamine, tert-butylamine etc.

An aryl group is to be understood as meaning a phenyl or naphthyl group.

A heteroaryl group is to be understood as meaning a mono- or bi-cyclic aromatic group containing from 5 to 13 chain members and from one to four hetero atoms selected from nitrogen, oxygen and sulphur, for example a furyl, pyridyl or thienyl group.

The expression "optionally substituted" describing aryl and heteroaryl signifies that those groups are optionally substituted by one or more halogen atoms or linear or branched ($C_1$–$C_6$)-alkyl, hydroxy, linear or branched ($C_1$–$C_6$)-alkoxy, linear or branched ($C_1$–$C_6$)-perhaloalkyl, cyano, nitro, sulfo, amino, linear or branched ($C_1$–$C_6$)-acyl, acylamino, linear or branched ($C_1$–$C_6$)-alkylsulfonyl or linear or branched ($C_1$–$C_6$)-alkylsulpholamino groups.

The term "acyl", alone or in the expression "acylamino", represents a linear or branched ($C_1$–$C_6$)-alkylcarbonyl group or a ($C_3$–$C_8$)-cycloalkylcarbonyl group.

Preferably, the invention relates to compounds of formula (I) wherein m and n are each 1.

Other preferred compounds of the invention are those wherein m is 3 while n is 0.

In compounds of formula (I), X preferably represents a cyano group.

In preferred compounds of the invention, A represents a σ bond or an NR—CO— or NR—SO$_2$ group, R preferably being a hydrogen atom.

In compounds of formula (I), $R_1$ and $R_2$ each more especially represents a hydrogen atom.

Preferred $R_3$ groups of the invention are optionally substituted phenyl or optionally substituted biphenyl groups.

Another preferred group $R_3$ is an aryl group (more especially phenyl) substituted by a group A'—Cy wherein A' preferably represents an NR—CO or NR—SO$_2$ group (R being more especially a hydrogen atom) and Cy preferably represents an optionally substituted aryl group.

Another preferred $R_3$ group is the group 2-indolinon-5-yl.

The invention relates more preferably to compounds of formula (I) wherein X represents a cyano group, m and n are each 1, $R_1$ and $R_2$ each represent a hydrogen atom, and p is 4 when A represents an NHCO group and $R_3$ represents an optionally substituted phenyl group or an optionally substituted biphenyl group, or p is 1 or 2 when A represents a σ bond and $R_3$ represents an optionally substituted phenyl group or an optionally substituted biphenyl group.

The invention extends also to a process for the preparation of compounds of formula (I) which is characterised in that there is used as starting material a compound of formula (II):

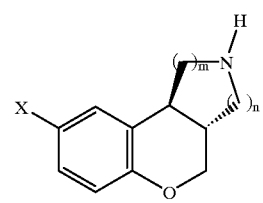

wherein X, m and n are as defined for formula (I), which is treated with a compound of formula (III):

wherein G represents a halogen atom or a CHO group, q is an integer such that $0 \leq q \leq 6$, and $R_1$, $R_2$ and $R_3$ are as defined for formula (I), to yield, after reduction when G represents a CHO group, a compound of formula (I/a):

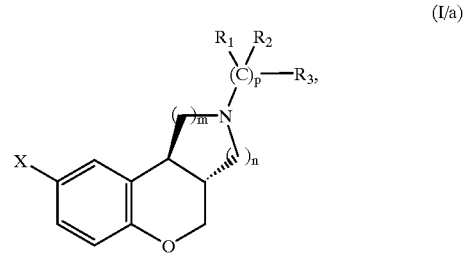

a particular case of compounds of formula (I) wherein X, $R_1$, $R_2$, $R_3$, m, n and p are as defined for formula (I), or with a compound of formula (IV):

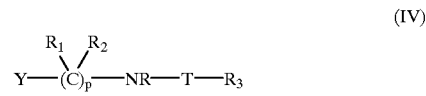

wherein Y represents a halogen atom, R, $R_1$, $R_2$, $R_3$ and p are as defined for formula (I) and T represents a CO or SO$_2$ group, to yield a compound of formula (I/b):

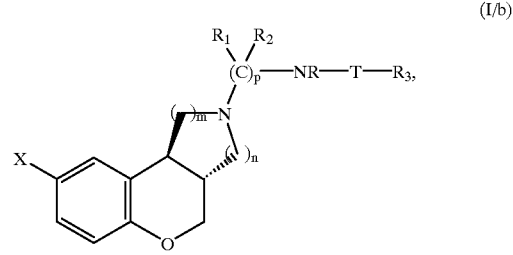

a particular case of compounds of formula (I) wherein X, R, $R_1$, $R_2$, $R_3$, m, n and p are as defined for formula (I) and T is as defined above, or with a compound of formula (V):

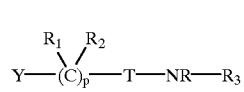
(V)

wherein Y represents a halogen atom, R, $R_1$, $R_2$, $R_3$ and p are as defined for formula (I) and T represents a CO or $SO_2$ group, to yield a compound of formula (I/c):

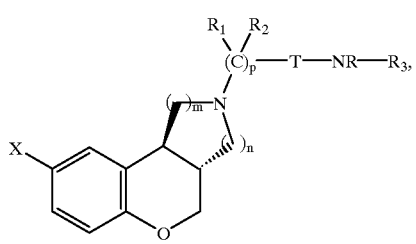
(I/c)

a particular case of compounds of formula (I) wherein X, R, $R_1$, $R_2$, $R_3$, m, n and p are as defined for formula (I) and T is as defined above, or with a compound of formula (III'):

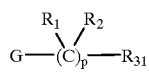
(III')

wherein G represents a halogen atom or a CHO group, p, $R_1$ and $R_2$ are as defined for formula (I) and $R_{31}$ represents an aryl or heteroaryl group substituted by a halogen atom or by a carboxy, nitro or sulpho group, to yield a compound of formula (I'/a):

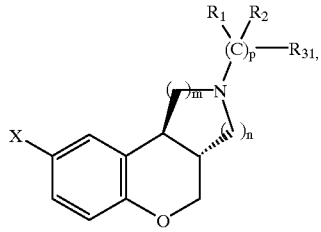
(I'/a)

a particular case of compounds of formula (I/a) wherein X, $R_1$, $R_2$, $R_{31}$, m, n and p are as defined hereinbefore, which:

when $R_{31}$ represents an aryl or heteroaryl group substituted by a halogen atom, is treated with an appropriate vinyl compound, tin compound or boronic acid compound in the presence of a palladium catalyst to yield a compound of formula (I/d):

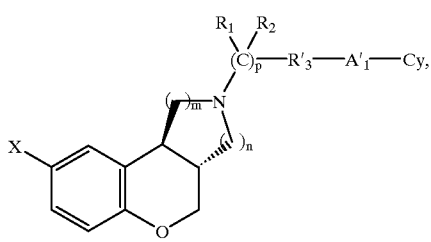
(I/d)

a particular case of compounds of formula (I) wherein X, $R_1$, $R_2$, $R_{31}$, m, n and p are as defined hereinbefore, $R'_3$ represents an aryl or heteroaryl group, $A'_1$, represents a a bond, an alkylene group (in which a carbon atom may optionally be replaced by an oxygen or sulphur atom) or an alkenylene group (in which a carbon atom may optionally be replaced by an oxygen or sulphur atom) and Cy is as defined for formula (I), when $R_{31}$ represents an aryl or heteroaryl group substituted by a nitro group, after reduction of that group to amine, is treated with a compound of formula Cl—CO—Cy or Cl—$SO_2$—Cy to yield a compound of formula (I/e):

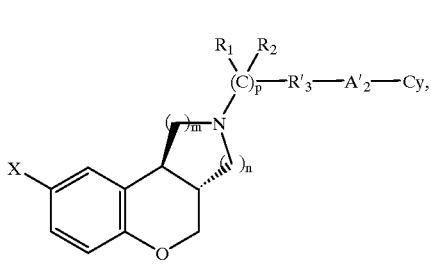
(I/e)

a particular case of compounds of formula (I) wherein X, $R_1$, $R_2$, m, n, p and Cy are as defined for formula (I), $R'_3$ represents an aryl or heteroaryl group and $A'_2$ represents an —NR—CO or —NR—$SO_2$— group (R being as defined for formula (I)), when $R_{31}$, represents an aryl or heteroaryl group substituted by a sulpho or carboxy group, is treated with a compound of formula HNR—Cy to yield a compound of formula (I/f):

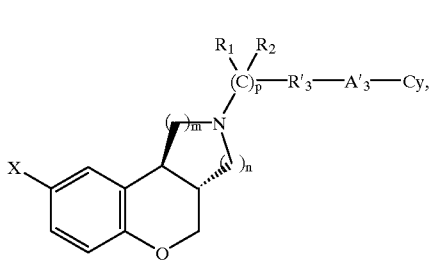
(I/f)

a particular case of compounds of formula (I) wherein X, $R_1$, $R_2$, m, n, p and Cy are as defined for formula (I), $R'_3$ represents an aryl or heteroaryl group and $A'_3$ represents a —CO—NR— or —$SO_2$—NR— group (R being as defined hereinbefore), which compounds of formulae (I/a) to (I/f):
  are purified, if necessary, according to a conventional purification technique,
  are separated, where appropriate, into the enantiomers according to a conventional separation technique,
  are converted, if desired, into addition salts with a pharmaceutically acceptable acid or base,
  with the proviso that when X represents a CN group it may be converted into an aminoalkyl group according to conventional techniques of organic chemistry at any stage of the synthesis.

With the aim of providing a synthesis better adapted to certain products of formula (I) it is desired to obtain, it shall be possible for certain variants of the above-described process to be used.

One such variant comprises using as starting material a compound of formula (VI):

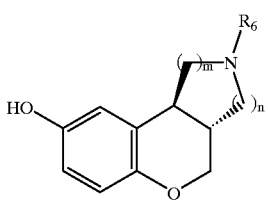

(VI)

wherein m and n are as defined for formula (I) and $R_6$ represents a linear or branched $(C_1-C_6)$-alkyl group,
  which is treated with trifluoromethanesulphonic anhydride to yield a compound of formula (VII):

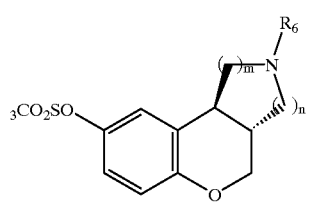

(VII)

wherein $R_6$, m and n are as defined hereinbefore,
  which compound of formula (VII) reacts with tributyltin cyanide in the presence of lithium chloride and a palladium(0) catalyst to yield a compound of formula (I/g):

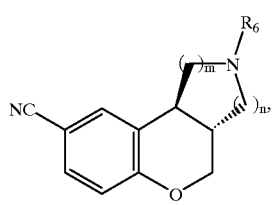

(I/g)

a particular case of compounds of formula (I) wherein $R_6$, m and n are as defined hereinbefore,
  which compound of formula (I/g) may, if necessary, be purified by conventional purification methods and may, where appropriate, be separated into the enantiomers by a conventional separation technique and may, if desired, be converted into an addition salt with a pharmaceutically acceptable acid or base.

The present invention relates also to the use, for the manufacture of pharmaceutical compositions for use in the treatment of disorders requiring a $D_3$ receptor ligand, of compounds of formula (VIII):

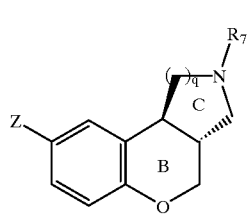

(VIII)

wherein:
  q represents 1 or 2,
  Z represents a cyano or aminocarbonyl group,
  $R_7$ represents a linear or branched $(C_1-C_6)$-alkyl group, a benzyl group or an acylamino-$(C_1-C_6)$-alkyl group (in which the alkyl moiety is linear or branched and in which the acyl group is a benzoyl, naphthylcarbonyl, thienylcarbonyl, furylcarbonyl, pyrrolylcarbonyl or pyridinylcarbonyl group each of which is optionally substituted by one or more halogen atoms or trihalomethyl, alkoxy or hydroxy groups),
  the junction between the rings B and C is in the trans configuration,
compounds (VIII) being described in the application EP 691 342.

The invention extends also to pharmaceutical compositions comprising as active ingredient at least one compound of formula (I), alone or in combination with one or more inert, non-toxic excipients or carriers.

Among the pharmaceutical compositions according to the invention there may be mentioned more especially those which are suitable for oral, parenteral or nasal administration, tablets or dragees, sublingual tablets, gelatin capsules, lozenges, suppositories, creams, ointments, dermal gels etc.

The useful dosage varies according to the age and weight of the patient, the nature and severity of the disorder and the administration route, which may be nasal, rectal, parenteral or oral. Generally, the unit dose ranges from 1 to 500 mg for a treatment of from 1 to 3 administrations per 24 hours.

The Examples which follow illustrate the invention and do not limit it in any way. The structures of the described compounds were confirmed by customary spectroscopic techniques.

The Preparations described below lead to the starting materials used in the synthesis of the compounds of the invention.

PREPARATION A: 3-Nitrophenylacetaldehyde 90 mmol of iodoxybenzoic acid are added to 60 mmol of 2-(3-nitrophenyl)ethanol in 300 ml of tetrahydrofuran. The reaction mixture is heated at reflux for 4 hours, then cooled and filtered. The filtrate is concentrated to yield the expected compound.

PREPARATION B: N-[4-(2-Chloroethyl)phenyl]acetamide
  Step a: N-(4-Chloroacetylphenyl)acetamide 23.5 mmol of chloroacetyl chloride and, in portions, 18.1 mmol of acetanilide, are added slowly, under an argon atmosphere, to 108 mmol of aluminium chloride in 90 ml of 1,2-dichloroethane. The reaction mixture is heated at 60° C. for 2 hours and then cooled with an ice bath. After slow hydrolysis using ice, and filtration, the precipitate obtained is washed with ethyl ether and dried. The expected product so obtained is used in the following without being purified.

Step b : N-[4-(2-Chloroethyl)phenyl]acetamide 22.7 mmol of triethylsilane are slowly added to 11.1 mmol of the product obtained in the above Step dissolved in 10 ml of trifluoroacetic acid. Stirring is maintained for 24 hours. The trifluoroacetic acid is then removed and the residue obtained is taken up in 50 ml of acetonitrile and then washed with hexane (4 times 30 ml). After concentration, the expected product is purified by chromatography on silica gel using a 90/10 dichloromethane/ethyl acetate mixture as eluant.

PREPARATION C: 5-(2-Chloroethyl)-1,3-dihydro-2-oxo-indole

Step a :5-Chloroacetyl-1,3-dihydro-2-oxo-indole

The expected product is obtained in accordance with the process described in Preparation B, Step a, replacing the acetanilide with 1,3-dihydro-2-oxo-indole.

Step b: 5-(2-Chloroethyl)-1,3-dihydro-2-oxo-indole

The expected product is obtained in accordance with the process described in Preparation B, Step b, starting from the compound obtained in the above Step.

PREPARATION D: 4-Cyano-N-(4-hydroxybutyl)benzamide 100 mmol (9.2 ml) of 4-aminobutanol are slowly added, at a temperature of 5° C., to 100 mmol (16.56 g) of 4-cyanobenzoyl chloride in 400 ml of dichloromethane. While maintaining the temperature at 5° C., 100 mmol (13.9 ml) of triethylamine are added. The reaction mixture is stirred for 15 hours at room temperature before being hydrolysed. The organic phase is then decanted off and washed with a 1N hydrochloric acid solution. After evaporating off the solvent, the residue obtained is purified by chromatography on silica gel using a 97/3 dichloromethane/methanol mixture as eluant to yield the expected product.

PREPARATION E: 4-Phenyl-N-(4-hydroxybutyl)benzamide

The expected product is obtained in accordance with the process described in Preparation D, replacing the 4-cyanobenzoyl chloride with 4-phenylbenzoyl chloride.

PREPARATION F: 4-Bromo-N-(4-hydroxybutyl)benzamide

The expected product is obtained in accordance with the process described in Preparation D, replacing the 4-cyanobenzoyl chloride with 4-bromobenzoyl chloride.

PREPARATION G: 4-Fluoro-N-(4-hydroxybutyl)benzamide

The expected product is obtained in accordance with the process described in Preparation D, replacing the 4-cyanobenzoyl chloride with 4-fluorobenzoyl chloride.

PREPARATION H: N-(4-Hydroxybutyl)-2-trifluoromethylbenzamide

The expected product is obtained in accordance with the process described in Preparation D, replacing the 4-cyanobenzoyl chloride with 2-trifluoromethylbenzoyl chloride.

PREPARATION I: N-(4-Bromophenyl)-5-chloropentanamide 366 mmol (26.7 ml) of thionyl chloride are added dropwise to 183 mmol (25 g) of 5-chlorovaleric acid in 250 ml of toluene heated at reflux. The mixture is stirred at reflux until the evolution of gas has ceased and is then cooled. The solvent is evaporated off. The product obtained is then redissolved in 250 ml of dichloromethane and the temperature is lowered to 5° C. A solution of 183 mmol (31.5 g) of 4-bromoaniline in 100 ml of dichloromethane and 183 mmol (25.5 ml) of triethylamine are added in succession. The reaction mixture is stirred for 4 hours at 5° C. and then for 15 hours at room temperature. Hydrolysis, washing the organic phase with a 1N hydrochloric acid solution and evaporating off the solvents yields the expected product, which is used without being purified.

PREPARATION J: 4-Phenylbenzaldehyde 65 mmol of 4-benzylpyridinium dichromate are added to 54 mmol of 4-phenylbenzyl alcohol in 400 ml of dichloromethane. The reaction mixture is stirred for 2 hours at room temperature. 600 ml of a mixture of ethyl ether and hexane in a ratio of 1 to 1 are added. After stirring for 30 minutes, the mixture is filtered. The filtrate is washed once with 100 ml of a 1N hydrochloric acid solution. The organic phase is dried over magnesium sulphate and then concentrated to yield the expected compound.

PREPARATION K: 4-Biphenylacetaldehyde

The expected product is obtained in accordance with the process described in Preparation A, replacing the 2-(3-nitrophenyl)ethanol with 2-(4-biphenyl)ethanol.

PREPARATION L: 4-Bromophenylacetaldehyde

The expected product is obtained in accordance with the process described in Preparation A, replacing the 2-(3-nitrophenyl)ethanol with 4-bromophenylethanol.

PREPARATION M: 4-Nitrophenylacetafdehyde

The expected product is obtained in accordance with the process described in Preparation A, replacing the 2-(3-nitrophenyl)ethanol with 2-(4-nitrophenyl)ethanol.

PREPARATION N: 4-Bromo-N-(4-hydroxybutyl)benzenesulphonamide

The expected product is obtained in accordance with the process described in Preparation D, replacing the 4-cyanobenzoyl chloride with 4-bromobenzenesulphonyl chloride.

PREPARATION O: 4-Fluoro-N-(4-hydroxypropyl)benzamide

The expected product is obtained in accordance with the process described in Preparation G, replacing the 4-aminobutanol with 3-aminopropanol.

PREPARATION P: 4-Acetylbenzoyl chloride 120 mmol of thionyl chloride are added to 600 mmol of 4-acetylbenzoic acid in 150 ml of toluene. The reaction mixture is heated at reflux for 3 hours and then cooled. The solvent is evaporated off. The product is used without any other treatment.

PREPARATION Q: 4-Cyano-N-(4-hydroxybutyl)-1-methoxy-2-naphthylamide

Step a: Methyl 2-(1-hydroxy)naphthoate 500 mmol of O-methylcaprolactim are added to 500 mmol of 1-hydroxy-2naphthoic acid. The mixture is heated at 85° C. for 15 hours and then cooled. After the addition of 50 ml of ethyl ether and adjustment of the pH to 9–10, the mixture is extracted with ethyl ether. The organic phases are combined and dried over magnesium sulphate. The expected product is precipitated from isopropyl ether and isolated by filtration.

Step b: Methyl 2-(4-bromo-1-hydroxy)naphthoate 440 mmol of bromine are slowly added to 370 mmol of the compound obtained in Step a. The mixture is stirred for 3 hours at room temperature before being diluted with water. The precipitate formed is washed with water, filtered and dried to yield the expected product.

Step c: Methyl 2-(4-bromo-1-methoxy)naphthoate 350 mmol of the compound obtained in Step b are added to 530 mmol of potassium carbonate in 2 liters of acetone. 590 mmol of dimethyl sulphate are then added. The reaction mixture is heated at reflux for 4 hours and then filtered. The filtrate is concentrated. The residue is taken up in isopropyl ether and the precipitate formed is filtered to yield the expected compound.

Step d: Methyl 2-(4-cyano-1-methoxy)naphthoate 110 mmol of the compound obtained in the above Step, 70 mmol of zinc cyanide and 7 mmol of tetrakis(triphenylphosphine)palladium are added to 120 ml of dimethylformamide. The reaction mixture is heated at 80° C. for 5 hours and then cooled and diluted with dichloromethane. The organic phase is washed with a 2N ammonium hydroxide solution and then dried over magnesium sulphate. The expected product is obtained after purification by chromatography on silica gel.

Step e: 2-(4-Cyano-1-methoxy)naphthoic acid 32 mmol of the compound obtained in the above Step are dissolved in 80 ml of water plus 80 ml of tetrahydrofuran. 36 mmol of lithium hydroxide are then added. After 2 hours the tetrahydrofuran is evaporated off. The aqueous phase is washed with ethyl ether and then adjusted to pH 3. The precipitate obtained is filtered off and washed with water to neutral pH, and is then dried to yield the expected product.

Step f: 2-(4-Cyano-1-methoxy)naphthoic acid chloride

The expected product is obtained in accordance with the process described in Preparation P, replacing the 4-acetylbenzoic acid with the compound obtained in the above Step.

Step g: 4-Cyano-N-(4-hydroxybutyl)-1-methoxy-2-naphthylamide

The expected product is obtained in accordance with the process described in Preparation D, replacing the 4-cyanobenzoyl chloride with the compound obtained in the above Step.

PREPARATION R: 4-Fluoro-N-(2-hydroxyethyl)benzamide

The expected product is obtained in accordance with the process described in Preparation G, replacing the 4-aminobutanol with 2-aminoethanol.

PREPARATION S: 4-Phenyl-N-(2-hydroxyethyl)benzamide

The expected product is obtained in accordance with the process described in Preparation E, replacing the 4-aminobutanol with 2-aminoethanol.

PREPARATION T: 4-Methoxy-N-(4-hydroxybutyl)benzenesulphonamide

The expected product is obtained in accordance with the process described in Preparation D, replacing the 4-cyanobenzoyl chloride with 4-methoxybenzenesulphonyl chloride.

PREPARATION U: 4-Nitro-N-(4-hydroxybutyl)benzenesulphonamide

The expected product is obtained in accordance with the process described in Preparation D, replacing the 4-cyanobenzoyl chloride with 4-nitrobenzenesulphonyl chloride.

PREPARATION V: 4-Bromo-N-(3-hydroxypropyl)benzenesulphonamide

The expected product is obtained in accordance with the process described in Preparation N. replacing the 4-aminobutanol with 3-aminopropanol.

PREPARATION W: 4-Nitro-N-(3-hydroxypropyl)benzenesulphonamide

The expected product is obtained in accordance with the process described in Preparation U, replacing the 4-aminobutanol with 3-aminopropanol.

PREPARATION X: 4-Bromo-N-(2-hydroxyethyl)benzenesulphonamide

The expected product is obtained in accordance with the process described in Preparation N, replacing the 4-aminobutanol with 2-aminoethanol.

PREPARATION Y: 4-Methoxy-N-(2-hydroxyethyl)benzenesulphonamide

The expected product is obtained in accordance with the process described in Preparation T, replacing the 4-aminobutanol with 2-aminoethanol.

EXAMPLE 1

(4aα, 10bβ)-9-Cyano-4-propyl-1,3,4,4a,5,10b-hexahydro-2H-chromeno[3,4-b]pyridine Hydrochloride Step a: (4aα, 10bβ)-9-hydroxy-4-propyl-1,3,4,4a,5,10b-hexahydro-2H-chromeno[3,4-b]pyridine Methanesulphonate To 6.4 mmol of 9-hydroxy-4-propyl-1,3,4,4a,5,10b-hexahydro-2H-chromeno[3,4-b]pyridine (described in J. Med. Chem., 1989, 32, 720–7) dissolved in 100 ml of dichloromethane and cooled to −30° C. there are added, in succession, 9.7 mmol of 2,6-lutidine, 1.3 mmol of 4-dimethylaminopyridine and 9.7 mmol of triflic anhydride dropwise. After 30 minutes' stirring, the mixture is hydrolysed with a saturated NaCl solution. The organic phase is then decanted off and subsequently concentrated, and the expected product is purified by chromatography on silica gel.

Step b: (4aα, 10bβ)-9-Cyano-4-propyl-1,3,4,4a,5,10b-hexahydro-2H-chromeno[3,4-b]pyridine Hydrochloride 5.4 mmol of tributyltin cyanide, 7.8 mmol of lithium chloride and 2.6 mmol of tetrakis(triphenylphosphine)palladium are added in succession to 2.6 mmol of the compound prepared in the above Step in 20 ml of 1,2-dichloroethane. The reaction mixture is heated at reflux for 18 hours. After cooling and hydrolysis with a saturated potassium fluoride solution, the mixture is filtered. The organic phase is decanted off and concentrated. The expected product is obtained by purification by chromatography on silica gel.

The corresponding hydrochloride is obtained by the action of a titrated solution of hydrochloric acid in ethanol.

Elemental Microanalysis:

|  | C | H | Cl | N |
|---|---|---|---|---|
| % calculated | 65.63 | 7.23 | 12.11 | 9.57 |
| % found | 65.28 | 7.06 | 11.77 | 9.30 |

EXAMPLE 2

(3aα,9bβ)-8-Cyano-2-phenethyl-1,2,3,3a,4,9b-hexahydrochromeno[3,4-c]pyrrole Hydrochloride 10 mmol of potassium carbonate are added to 5 mmol of (3aα,9bβ)-8-cyano-1,2,3,3a,4,9b-hexahydrochromeno[3,4-c]pyrrole (described in application EP 691 342) in 50 ml of acetonitrile. The reaction mixture is stirred at room temperature for 15 minutes. 0.5 mmol of potassium iodide and 5 mmol of phenethyl bromide dissolved in 50 ml of acetonitrile are added in succession. The reaction mixture is then heated at reflux for 15 hours. After hydrolysis and extraction with dichloromethane, the organic phases are combined and concentrated. The expected product is obtained by purification by chromatography on silica gel using a 95/5 dichloromethane/methanol mixture as eluant. The product is converted into the corresponding hydrochloride using a solution of ethanol saturated with hydrochloric acid.

Elemental Microanalysis:

|  | C | H | Cl | N |
|---|---|---|---|---|
| % calculated | 70.48 | 6.21 | 10.40 | 8.22 |
| % found | 70.42 | 6.24 | 10.45 | 7.78 |

EXAMPLE 3

(3aα,9bβ)-8-Cyano-2-[2-(3-methylsulphonylaminophenyl)ethyl]-1,2,3,3a,4,9b-hexahydrochromeno[3,4-c]pyrrole Hydrochloride Step a: (3aα, 9bβ)-8-Cyano-2-[2-(3-nitrophenyl)ethyl]-1,2,3,3a,4,9b-hexahydrochromeno[3,4-c]pyrrole 30 mmol of (3aα, 9bβ)-8-cyano-1,2,3,3a,4,9b-hexahydrochromeno[3,4-c]pyrrole (described in application EP 691 342) and then 30 mmol of acetic acid are added to 60 mmol of the compound described in Preparation A in 500 ml of 1,2-dichloroethane. After 10 minutes, 42 mmol of sodium triacetoxyborohydride are added. The reaction mixture is stirred at room temperature for 15 hours, then washed with a saturated sodium hydrogen carbonate solution. The organic phase is decanted off, dried and concentrated. The expected product is obtained by purification by chromatography on silica gel using a 97/3 toluene/ethanol mixture as eluant.

Step b: (3aα, 9bβ)-8-Cyano-2-[2-(3-aminophenyl)ethyl]-1,2,3,3a,4,9b-hexahydrochromeno[3,4-c]pyrrole 0.6 g of 10% palladium-on-carbon are added to 9 mmol of the compound obtained in the above Step in 300 ml of ethanol. The reaction mixture is placed under a hydrogen atmosphere for 1 hour 30 minutes. The expected product is obtained after filtering off the catalyst and concentrating the filtrate.

Step c: (3aα, 9bβ)-8-Cyano-2-[2-(3-methylsulphonylaminophenyl)ethyl]-1,2,3,3a,4,9b-hexahydrochromeno[3,4-c]pyrrole Hydrochlorde 9 mmol of the compound obtained in Step b dissolved in dichloromethane are added at −5° C. to 10 mmol of methanesulphonyl chloride in 15 ml of dichloromethane. After 15 hours' stirring at room temperature, the mixture is treated with 1N sodium hydroxide solution. The organic phase is decanted off, dried and concentrated. The expected product is obtained by purification by chromatography on silica gel using a 95/5 dichloromethane/methanol mixture as eluant. The corresponding hydrochloride is obtained by the action of a titrated solution of hydrochloric acid in ethanol.

Elemental Microanalysis:

|  | C | H | Cl | N | S |
|---|---|---|---|---|---|
| % calculated | 58.12 | 5.57 | 8.17 | 9.68 | 7.39 |
| % found | 58.56 | 5.85 | 8.25 | 9.37 | 6.98 |

EXAMPLE 4

(3aα,9bβ)-2-[2-(4-Acetylaminophenyl)ethyl]-8-cyano-1,2,3,3a,4,9b-hexahydrochromeno[3,4-c]pyrrole Hydrochloride The expected product is obtained in accordance with the process described in Example 2, replacing the phenethyl bromide with the compound described in Preparation B.

Elemental Microanalysis

|  | C | H | Cl | N |
|---|---|---|---|---|
| % calculated | 66.41 | 6.08 | 8.91 | 10.56 |
| % found | 66.35 | 6.10 | 8.89 | 10.25 |

EXAMPLE 5

(3aα,9bβ)-8-Cyano-2-[2-(2-oxo-2,3-dihydro-1H-indol-5-yl)ethyl]-1,2,3,3a,4,9b-hexahydrochromeno[3,4-c]pyrrole Hydrochloride The expected product is obtained in accordance with the process described in Example 2, replacing the phenethyl bromide with the compound described in Preparation C.

Elemental Microanalysis:

|  | C | H | Cl | N |
|---|---|---|---|---|
| % calculated | 66.75 | 5.60 | 8.96 | 10.61 |
| % found | 66.24 | 5.77 | 8.51 | 10.45 |

EXAMPLE 6

(3aα,9bβ)-2-(4-Bromobenzyl)-8-cyano-1,2,3,3a,4,9b-hexahydrochromeno[3,4-c]pyrrole Hydrochloride The expected product is obtained in accordance with the process described in Example 2, replacing the phenethyl bromide with 4romobenzyl bromide.

Elemental Microanalysis:

|  | C | H | Cl | N |
|---|---|---|---|---|
| % calculated | 56.25 | 4.47 | 8.74 | 6.90 |
| % found | 56.50 | 4.74 | 8.37 | 6.45 |

EXAMPLE 7

(3aα,9bβ)-2-(4-Acetylaminobenzyl)-8-cyano-1,2,3,3a,4,9b-hexahydrochromeno[3,4-c]pyrrole Hydrochloride The expected product is obtained using the process described in Example 3, Step a, replacing the product of Preparation A with 4-acetylaminobenzaldehyde.

EXAMPLE 8

(3aα,9bβ)-8-Cyano-(4-fluorobenzyl)-1,2,3,3a,4,9b-hexahydrochromeno[3,4-c]pyrrole Hydrochloride The expected product is obtained using the process described in Example 3, Step a, replacing the product of Preparation A with 4-fluorobenzaldehyde.

EXAMPLE 9

(3aα,9bβ)-8-Cyano-(3-nitrobenzyl)-1,2,3,3a,4,9b-hexahydrochromeno[3,4-c]pyrrole Hydrochloride The expected product is obtained using the process described in Example 2, replacing the phenethyl bromide with 3-nitrobenzyl bromide.

EXAMPLE 10

(3aα,9bβ)-2-Benzyl-8-cyano-1,2,3,3a,4,9b-hexahydrochromeno-[3,4-c]pyrrole Hydrochloride The product is described in Example 29 of the application EP 691 342.

EXAMPLE 11

(3aα,9bβ)-8-Aminocarbonyl-2-benzyl-1,2,3,3a,4,9b-hexahydrochromeno[3,4-c]pyrrole Hydrochloride 40 g of polyphosphoric acid are added to 15 mmol of the compound described in Example 10. The mixture is heated at 140° C. for 4 hours and then poured into an ice bath. The pH is adjusted to 12 by the addition of a concentrated aqueous NaOH solution. After the addition of 1 liter of water and 300 ml of dichloromethane, the biphasic mixture is stirred for 15 hours and then decanted. After extraction, the organic phase is dried and concentrated. The expected product is obtained by purification by chromatography on silica gel using a 96/4/0.4 dichloromethane/methanol/ammonium hydroxide mixture as eluant. The corresponding hydrochloride is obtained by the action of a titrated solution of hydrochloric acid in ethanol.

Elemental Microanalysis:

|  | C | H | Cl | N |
|---|---|---|---|---|
| % calculated | 66.18 | 6.14 | 10.28 | 8.12 |
| % found | 65.64 | 6.16 | 10.01 | 7.84 |

EXAMPLE 12

(3aα,9bβ)8-Cyano-2-propyl-1,2,3,3a,4,9b-hexahydrochromeno-[3,4-c]pyrrole Hydrochloride The product is described in Example 31 of application EP 691 342.

EXAMPLE 13

4-Cyano-N-[4-((3aα,9bβ)-8-cyano-1,2,3,3a,4,9b-hexahydrochromeno[3,4-c]pyrrol-2-yl)butyl]benzamide Hydrochloride At −60° C., 20 mmol of dimethyl sulphoxide dissolved in 12 ml of dichloromethane are added to 20 mmol of oxalyl chloride dissolved in 48 ml of dichloromethane. A solution of the compound described in Preparation D in 32 ml of dichloromethane is slowly added. The reaction mixture is maintained at −60° C. for 45 minutes, then 50 mmol of triethylamine are slowly added. The reaction mixture is allowed to return to room temperature. After hydrolysis and extraction with dichloromethane, the organic phase is washed with a saturated solution of sodium chloride and concentrated. The product obtained is redissolved in 50 ml of 1,2-dichloroethane and then 10 mmol of (3aα,9bβ)-8-cyano-1,2,3,3a,4,9b-hexahydrochromeno[3,4-c]pyrrole (described in application EP 691 342) and 10 mmol of acetic acid are added in succession. After 10 minutes' stirring, 17.5 mmol of sodium triacetoxyborohydride are added. Stirring is maintained for 15 hours and then the mixture is hydrolysed with a saturated solution of sodium hydrogen carbonate. After extraction with dichloromethane, the expected product is obtained by purification by chromatography on silica gel using a 95/5 dichloromethane/methanol mixture as eluant. The corresponding hydrochloride is obtained by the action of a solution of ethanol saturated with hydrochloric acid.

Elemental Microanalysis:

|  | C | H | Cl | N |
|---|---|---|---|---|
| % calculated | 65.97 | 5.77 | 8.11 | 12.82 |
| % found | 66.67 | 5.79 | 8.16 | 12.73 |

EXAMPLE 14

N-[4-((3aα,9bβ)-8-Cyano-1,2,3,3a,4,9b-hexahydrochromeno[3,4-c]pyrrol-2-yl)butyl]-4-phenylbenzamide Hydrochloride The expected product is obtained in accordance with the process described in Example 7, replacing the product of Preparation D with the compound described in Preparation E.

Elemental Microanalysis:

|  | C | H | Cl | N |
|---|---|---|---|---|
| % calculated | 71.37 | 6.20 | 7.26 | 8.61 |
| % found | 71.46 | 6.17 | 7.54 | 8.51 |

EXAMPLE 15

4-Bromo-N-[4-((3aα,9bβ)-8-cyano-1,2,3,3a,4,9b-hexahydrochromeno[3,4-c]pyrrol-2-yl)butyl]benzamide Hydrochloride The expected product is obtained in accordance with the process described in Example 13, replacing the product of Preparation D with the compound described in Preparation F.

Elemental Microanalysis:

|  | C | H | Br | Cl | N |
|---|---|---|---|---|---|
| % calculated | 56.28 | 5.13 | 16.28 | 7.22 | 8.56 |
| % found | 56.10 | 5.03 | 16.00 | 7.17 | 8.49 |

EXAMPLE 16

N-[4-((3aα, 9bβ)-8-Cyano-1,2,3,3a,4,9b-hexahydrochromeno[3,4-c]pyrrol-2-yl)butyl]-4-fluorobenzamide Hydrochloride The expected product is obtained in accordance with the process described in Example 13, replacing the product of Preparation D with the compound described in Preparation G.

Elemental Microanalysis:

|           | C     | H    | Cl   | N    |
|-----------|-------|------|------|------|
| % calculated | 64.26 | 5.86 | 8.25 | 9.77 |
| % found      | 64.08 | 5.93 | 8.69 | 9.62 |

EXAMPLE 17

N-[4-((3aα,9bβ)-8-Cyano-1,2,3,3a,4,9b-hexahydrochromeno[3,4-c]pyrrol-2-yl)butyl]-2-trifluoromethylbenzamide Hydrochloride The expected product is obtained in accordance with the process described in Example 13, replacing the product of Preparation D with the compound described in Preparation H.

Elemental Microanalysis:

|           | C     | H    | Cl   | N    |
|-----------|-------|------|------|------|
| % calculated | 60.06 | 5.25 | 7.39 | 8.76 |
| % found      | 60.47 | 5.15 | 7.36 | 8.87 |

EXAMPLE 18

N-(4-Bromophenyl)-5-[(3aα,9bβ)-8-cyano-1,2,3,3a,4,9b-hexahydrochromeno[3,4-c]pyrrol-2-yl]pentanamide Hydrochloride The expected product is obtained in accordance with the process described in Example 2, replacing the phenethyl bromide with the compound described in Preparation I.

EXAMPLE 19

(3aα,9bβ)-8-Aminocarbonyl-2-[2-(2-oxo-2,3-dihydro-1H-indol-5-yl) ethyl]-1,2,3,3a,4,9b-hexahydrochromeno[3,4-c]pyrrole Hydrochloride The expected product is obtained in accordance with the process described in Example 11, replacing the compound of Example 10 with the product described in Example 5.

Elemental Microanalysis:

|           | C     | H    | Cl   | N     |
|-----------|-------|------|------|-------|
| % calculated | 63.52 | 5.92 | 8.60 | 9.98  |
| % found      | 63.84 | 5.84 | 8.52 | 10.15 |

EXAMPLE 20

(3aα,9bβ)-8-Cyano-2-(4-phenylbenzyl)-1,2,3,3a,4,9b-hexahydrochromeno[3,4-c]pyrrole Hydrochloride The expected product is obtained in accordance with the process described in Example 3, Step a, replacing the product of Preparation A with that of Preparation J. The product is converted into the corresponding hydrochloride using a titrated solution of hydrochloric acid in ethanol.

Elemental Microanalysis:

|           | C     | H    | Cl   | N    |
|-----------|-------|------|------|------|
| % calculated | 74.62 | 5.86 | 8.61 | 6.85 |
| % found      | 74.52 | 5.50 | 8.78 | 6.95 |

EXAMPLE 21

(3aα, 9bβ)-8-Cyano-2-[4-(4-fluorophenyl)benzyl]-1,2,3,3a,4,9b-hexahydrochromeno[3,4-c]pyrrole Hydrochloride 2.7 mmol of the compound of Example 6 in the form of its base, 2.7 ml of a 2M solution of sodium carbonate and 3 mmol of 4-fluorophenylboronic acid dissolved in 2 ml of ethanol are added to 100 mg of tetrakis(triphenylphosphine) palladium in 20 ml of toluene. The reaction mixture is heated at reflux for 3 hours and then cooled. 0.2 ml of a solution of 30% hydrogen peroxide in water is added. After 30 minutes' stirring, 50 ml of ethyl ether are added. The mixture is decanted and the aqueous phase is extracted once with ether. The organic phases are combined and washed with a saturated solution of sodium chloride and then dried over magnesium sulphate. The expected product is obtained after purification by chromatography on silica gel. The product is converted into the corresponding hydrochloride using a titrated solution of hydrochloric acid in ethanol.

Elemental Microanalysis:

|           | C     | H    | Cl   | N    |
|-----------|-------|------|------|------|
| % calculated | 71.19 | 5.36 | 8.48 | 6.69 |
| % found      | 71.34 | 5.27 | 8.42 | 6.66 |

EXAMPLE 22

(3aα,9bβ)-8-Cyano-2-[2-(4-biphenyl)ethyl]-1,2,3,3a,4,9b-hexahydrochromeno[3,4-c]pyrrole Hydrochloride The expected product is obtained in accordance with the process described in Example 3, Step a, replacing the product of Preparation A with that of Preparation K. The product is converted into the corresponding hydrochloride using a titrated solution of hydrochloric acid in ethanol.

Elemental Microanalysis:

|           | C     | H    | Cl   | N    |
|-----------|-------|------|------|------|
| % calculated | 74.67 | 6.06 | 8.51 | 6.76 |
| % found      | 74.90 | 6.04 | 8.50 | 6.72 |

EXAMPLE 23

(3aα,9bβ)-8-Cyano-2-[2-(4-bromophenyl)ethyl]-1,2,3,3a,4,9b-hexahydrochromeno[3,4-c]pyrrole Hydrochloride The expected product is obtained in accordance with the process described in Example 3, Step a, replacing the product of Preparation A with that of Preparation L and without the addition of acetic acid. The product is converted into the corresponding hydrochloride using a titrated solution of hydrochloric acid in ethanol.

Elemental Microanalysis:

|  | C | H | Cl | N |
|---|---|---|---|---|
| % calculated | 56.90 | 4.82 | 8.19 | 6.40 |
| % found | 57.23 | 4.80 | 8.45 | 6.67 |

EXAMPLE 24

(3aα,9bβ)-8-Cyano-2-[2-(4'-fluoro-4-biphenyl) ethyl]-1,2,3,3a,4,9b-hexahydrochromeno[3,4-c] pyrrole Hydrochloride The expected product is obtained in accordance with the process described in Example 21, replacing the compound of Example 6 with that of Example 23 in the form of its base.

Elemental Microanalysis:

|  | C | H | Cl | N |
|---|---|---|---|---|
| % calculated | 71.62 | 5.66 | 7.98 | 6.42 |
| % found | 71.79 | 5.56 | 8.15 | 6.44 |

EXAMPLE 25

(3aα,9bβ)-8-Cyano-2-(4-phenyloxybenzyl)-1,2,3,3a, 4,9b-hexahydrochromeno[3,4-c]pyrrole Hydrochloride The expected product is obtained in accordance with the process described in Example 3, Step a, replacing the product of Preparation A with 4-phenyloxybenzaldehyde. The product is converted into the corresponding hydrochloride using a titrated solution of hydrochloric acid in ethanol Elemental Microanalysis:

|  | C | H | Cl | N |
|---|---|---|---|---|
| % calculated | 71.46 | 5.58 | 8.58 | 6.77 |
| % found | 71.68 | 5.53 | 8.46 | 6.69 |

EXAMPLE 26

(3aα,9bβ)-2-(4-Benzyloxybenzyl)-8-cyano-1,2,3,3a, 4,9b-hexahydrochromeno[3,4-c]pyrrole Hydrochloride The expected product is obtained in accordance with the process described in Example 3, Step a, replacing the product of Preparation A with 4-benzyloxybenzaldehyde and without the addition of acetic acid. The product is converted into the corresponding hydrochloride using a titrated solution of hydrochloric acid in ethanol.

Elemental Microanalysis:

|  | C | H | Cl | N |
|---|---|---|---|---|
| % calculated | 71.90 | 5.91 | 8.22 | 6.42 |
| % found | 72.13 | 5.82 | 8.19 | 6.47 |

EXAMPLE 27

(3aα,9bβ)-8-Cyano-2-(2-furylmethyl)-1,2,3,3a,4,9b-hexahydrochromeno[3,4-c]pyrrole Hydrochloride The expected product is obtained in accordance with the process described in Example 3, Step a, replacing the product of Preparation A with 2-furaldehyde and without the addition of acetic acid. The product is converted into the corresponding hydrochloride using a titrated solution of hydrochloric acid in ethanol.

Elemental Microanalysis:

|  | C | H | Cl | N |
|---|---|---|---|---|
| % calculated | 64.32 | 5.48 | 11.33 | 8.53 |
| % found | 64.46 | 5.41 | 11.19 | 8.84 |

EXAMPLE 28

(3aα,9bβ)-2-(3-Bromobenzyl)-8-cyano-1,2,3,3a,4, 9b-hexahydrochromeno[3,4-c]pyrrole Hydrochloride The expected product is obtained in accordance with the process described in Example 3, Step a, replacing the product of Preparation A with 3bromobenzaldehyde and without the addition of acetic acid. The product is converted into the corresponding hydrochloride using a titrated solution of hydrochloric acid in ethanol.

Elemental Microanalysis:

|  | C | H | Cl | N |
|---|---|---|---|---|
| % calculated | 56.06 | 4.43 | 8.62 | 6.62 |
| % found | 56.25 | 4.47 | 8.74 | 6.90 |

EXAMPLE 29

(3aα,9bβ)-2-(2-Bromobenzyl)-8-cyano-1,2,3,3a,4, 9b-hexahydrochromeno[3,4-c]pyrrole Hydrochloride The expected product is obtained in accordance with the process described in Example 3, Step a, replacing the product of Preparation A with 2-bromobenzaldehyde and without the addition of acetic acid. The product is converted into the corresponding hydrochloride using a titrated solution of hydrochloric acid in ethanol.

Elemental Microanalysis:

|  | C | H | Cl | N |
|---|---|---|---|---|
| % calculated | 55.95 | 4.48 | 8.46 | 6.61 |
| % found | 56.25 | 4.47 | 8.74 | 6.90 |

EXAMPLE 30

(3aα,9bβ)-8-Cyano-2-[4-(2-thienyl)benzy]-1,2,3,3a,
4,9b-hexahydrochromeno[3,4-c]pyrrole
Hydrochloride The expected product is obtained in accordance with the process described in Example 21, replacing the 4-fluorophenylboronic acid with 2-thienylboronic acid.

Elemental Microanalysis:

|  | C | H | Cl | N |
|---|---|---|---|---|
| % calculated | 67.83 | 5.21 | 8.25 | 6.83 |
| % found | 67.55 | 5.18 | 8.67 | 6.85 |

EXAMPLE 31

(3aα, 9bβ)-8-Cyano-2-{4-[2-(4-methoxyphenyl)
vinyl]benzyl}-1,2,3,3a,4,9b-hexahydrochromeno[3,
4-c]pyrrole Hydrochloride 4 mmol of 4-methoxystyrene and then 3.9 ml of triethylamine are added to 4 mmol of the compound of Example 6, in the form of its base, in 40 ml of DMF. 0.2 mmol of palladium diacetate and 0.8 mmol of tri-orthotolylphosphine are added to the reaction mixture. The mixture is heated at 100° C. for 3 hours. After cooling and after the addition of water, the mixture is decanted. The aqueous phase is extracted twice with 50 ml of ether each time. The organic phases are combined and dried over magnesium sulphate. The expected product is obtained after purification by chromatography on silica gel. The corresponding hydrochloride is obtained by the action of a titrated solution of hydrochloric acid in ethanol.

Elemental Microanalysis:

|  | C | H | Cl | N |
|---|---|---|---|---|
| % calculated | 72.90 | 6.00 | 7.41 | 6.14 |
| % found | 73.27 | 5.93 | 7.72 | 6.10 |

EXAMPLE 32

(3aα, 9bβ)-8-Cyano-2-{4-[2-(4-methoxyphenyl)
ethyl]benzyl}-1,2,3,3a,4,9b-hexahydrochromeno[3,
4-c]pyrrole Hydrochloride 4 mmol of the compound of Example 31 are dissolved in 150 ml of ethanol. After the addition of 100 mg of palladium-on-carbon, the mixture is stirred under atmospheric hydrogen pressure. After 2 hours at room temperature, the reaction mixture is filtered and the filtrate is then evaporated to yield the expected compound.

Elemental Microanalysis:

|  | C | H | Cl | N |
|---|---|---|---|---|
| % calculated | 72.82 | 6.39 | 7.81 | 6.01 |
| % found | 72.95 | 6.34 | 7.69 | 6.07 |

EXAMPLE 33

(3aα,9bβ)-8-Cyano-2-{2-[4-(2-thiényl)phenyl]
ethyl}-1,2,3,3a,4,9b-hexahydrochromeno[3,4-c]
pyrrole Hydrochloride The expected product is obtained in accordance with the process described in Example 30, replacing the compound of Example 6 with that of Example 23 in the form of its base.

Elemental Microanalysis:

|  | C | H | Cl | N |
|---|---|---|---|---|
| % calculated | 67.36 | 5.59 | 8.50 | 6.68 |
| % found | 67.22 | 5.64 | 8.62 | 6.81 |

EXAMPLE 34

(3aα,9bβ)-8-Cyano-2-[2-(4-
methylsulphonylaminophenyl)ethyl]-1,2,3,3a,4,9b-
hexahydrochromeno[3,4-c]pyrrole Hydrochloride The expected product is obtained in accordance with the process described in Example 3, replacing the compound of Preparation A in Step a with the compound described in Preparation M.

Elemental Microanalysis:

|  | C | H | Cl | N |
|---|---|---|---|---|
| % calculated | 58.12 | 5.57 | 8.17 | 9.68 |
| % found | 57.79 | 5.75 | 8.44 | 9.32 |

EXAMPLE 35

4-Bromo-N-{4-[(3aα,9bβ)-8-cyano-1,2,3,3a,4,9b-
hexahydrochromeno[3,4-c]pyrrol-2-yl]
butyl}benzenesulphonamide Hydrochloride The expected product is obtained in accordance with the process described in Example 13, replacing the product of Preparation D with the compound described in Preparation N.

EXAMPLE 36

N-[4-((3aα,9bβ)-8-Cyano-1,2,3,3a,4,9b-
hexahydrochromeno[3,4-c]pyrrol-2-yl)propyl]-4-
fluorobenzamide Hydrochloride The expected product is obtained in accordance with the process described in Example 13, replacing the product of Preparation D with the compound described in Preparation O.

Elemental Microanalysis:

|  | C | H | Cl | N |
|---|---|---|---|---|
| % calculated | 62.92 | 5.67 | 8.45 | 9.80 |
| % found | 63.54 | 5.57 | 8.52 | 10.10 |

EXAMPLE 37

4-Acetyl-N-{4-[2-(8-cyano-1,2,3,3a,4,9b-hexahydrochromeno [3,4-c]pyrrol-2-yl)ethyl) phenyl]benzamide Hydrochloride Step a: (3aα,9bβ)-8-Cyano-2-[2-(4-nitrophenyl)ethyl]-1,2, 3,3a,4,9b-hexahydrochromeno[3,4-c]pyrrole Hydrochloride The expected product is obtained in accordance with the process described in Example 3, Step a, replacing the product of Preparation A with that of Preparation M.

Step b. (3aα, 9bβ)-8-Cyano-2-[2-(4-aminophenyl)ethyl]-1, 2,3,3a,4,9b-hexahydrochromeno[3,4c]pyrrole The expected product is obtained in accordance with the process described in Example 3, Step b.

Step c: 4-Acetyl-N-{4-[2-(8-cyano-1,2,3,3a,4,9b-hexahydrochromeno[3,4-c]-pyrrol-2-yl)ethyl] phenyl}benzamide Hydrochloride The expected product is obtained in accordance with the process described in Example 3, Step c, replacing the methanesulphonyl chloride with the compound of Preparation P.

EXAMPLE 38

4-Cyano-1-methoxy-N-[4-(8-cyano-1,2,3,3a,4,9b-hexahydrochromeno[3,4-c]pyrrol-2-yl)butyl]-2-naphthylamide Hydrochloride The expected product is obtained in accordance with the process described in Example 13, replacing the product of Preparation D with the compound described in Preparation Q.

Elemental Microanalysis:

|  | C | H | Cl | N |
|---|---|---|---|---|
| % calculated | 67.42 | 5.61 | 6.78 | 10.52 |
| % found | 67.37 | 5.65 | 6.86 | 10.84 |

EXAMPLE 39

4-Fluoro-N-[2-((3aα,9bβ)-8-cyano-1,2,3,3a,4,9b-hexahydrochromeno[3,4-c]pyrrol-2-yl)ethyl] benzamide Hydrochloride The expected product is obtained in accordance with the process described in Example 13, replacing the product of Preparation D with the compound described in Preparation R.

EXAMPLE 40

4-Phenyl-N-[2-((3aα,9bβ)-8-cyano-1,2,3,3a,4,9b-hexahydrochromeno[3,4-c]pyrrol-2-yl)ethyl] benzamide Hydrochloride The expected product is obtained in accordance with the process described in Example 13, replacing the product of Preparation D with the compound described in Preparation S.

EXAMPLE 41

N-{4-[(3aα,9bβ)-8-cyano-1,2,3,3a,4,9b-hexahydrochromeno[3,4c]-pyrrol-2-yl]butyl}-4-methoxybenzenesulphonamide Hydrochloride The expected product is obtained in accordance with the process described in Example 13, replacing the product of Preparation D with the compound described in Preparation T.

EXAMPLE 42

N-{4-[(3aα,9bβ)-8-Cyano-1,2,3,3a,4,9b-hexahydrochromeno[3,4-c]pyrrol-2-yl]butyl}-4-nitrobenzenesulphonamide Hydrochloride The expected product is obtained in accordance with the process described in Example 13, replacing the product of Preparation D with the compound described in Preparation U.

EXAMPLE 43

4-Bromo-N-{3-[(3aα,4bβ)-8-cyano-1,2,3,3a,4,9b-hexahydrochromeno[3,4-c]pyrrol -2-yl] propyl}benzenesulphonamide Hydrochloride The expected product is obtained in accordance with the process described in Example 13, replacing the product of Preparation D with the compound described in Preparation V.

EXAMPLE 44

N-{3-[(3aα,9bβ)-8-Cyano-1,2,3,3a,4,9b-hexahydrochromeno[3,4-c]pyrrol-2-yl]propyl}-4-nitrobenzenesulphonamide Hydrochloride The expected product is obtained in accordance with the process described in Example 13, replacing the product of Preparation D with the compound described in Preparation W.

EXAMPLE 45

4-Bromo-N-{2-[(3aα,9bβ)-cyano-1,2,3,3a,4,9b-hexahydrochromeno[3,4-c]pyrrol-2-yl] ethyl}benzenesulphonamide Hydrochloride The expected product is obtained in accordance with the process described in Example 13, replacing the product of Preparation D with the compound described in Preparation X.

EXAMPLE 46

N-{2-[(3aα,9bβ)-8-Cyano-1,2,3,3a,4,9b-hexahydrochromeno[3,4-c]pyrrol-2-yl]ethyl}-4-methoxybenzenesulphonamide Hydrochloride The expected product is obtained in accordance with the process described in Example 13, replacing the product of Preparation D with the compound described in Preparation Y.

EXAMPLE 47

(3aα,9bβ)-8-Cyano-2-(2-pyridylmethyl)-1,2,3,3a,4, 9b-hexahydrochromeno[3,4-c]pyrrole Hydrochloride The expected product is obtained in accordance with the process described in Example 3, Step a, replacing the product of Preparation A with 2-pyridylcarboxaldehyde.

EXAMPLE 48

(3aα,9bβ)-2-[(6-[1,4]Benzodioxinyl)methyl]-8-cyano-1,2,3,3a,4,9b-hexahydrochromeno[3,4-c] pyrrole Hydrochloride The expected product is obtained in accordance with the process described in Example 3, Step a, replacing the product of Preparation A with 6-formyl[1,4]benzodioxin.

EXAMPLE 49

(3aα,9bβ)-2-[(5-Benzothienyl)methyl]-8-cyano-1,2,3,3a,4,9b-hexahydrochromeno[3,4-c]pyrrole Hydrochloride The expected product is obtained in accordance with the process described in Example 3, Step a, replacing the product of Preparation A with 5-formylbenzothiophene.

EXAMPLE 50

(3aα,9bβ)-8-Cyano-2-[2-(4-phenylsulphonylaminophenyl)ethyl]-1,2,3,3a,4,9b-hexahydrochromeno[3,4-c]pyrrole Hydrochloride The expected product is obtained in accordance with the process described in Example 3, replacing the methanesulphonyl chloride in Step c with benzenesulphonyl chloride.

EXAMPLE 51

(4aα,10bβ)-4-(4-Bromobenzyl)-9-cyano-1,3,4,4a,5,10b-hexahydro-2H-chromeno[3,4-b]pyridine Hydrochloride The expected product is obtained in accordance with the process described in Example 6, using as starting material 9cyano-1,3,4,4a,5,10b-hexahydro-2H chromeno-[3,4-c]pyridine (the latter having been prepared from the analogue hydroxylated in the 9 position described in J. Med. Chem., 1989, 32, 720).

EXAMPLE 52

(4aα,10bβ)-9-Cyano-4-[4-(4-fluorophenyl)benzyl]-1,3,4,4a,5,10b-hexahydro-2H-chromeno[3,4-b] pyridine Hydrochloride The expected product is obtained in accordance with the process described in Example 21, using as starting material the product of example 51.

EXAMPLE 53

(4aα,10bβ)-4-(4-Acetylaminobenzyl)-9-cyano-1,3,4,4a,5,10b-hexahydro-2H-chromeno[3,4-b]pyridine Hydrochloride The expected product is obtained in accordance with the process described in Example 7, using as starting material 9-cyano-1,3,4,4a,5,10hexahydro-2H-chromeno-[3,4-c]pyridine (the latter having been prepared from the analogue hydroxylated in the 9 position described in J. Med. Chem., 1989, 32, 720).

EXAMPLE 54

(4aα,10bβ)-4-[2-(4-Acetylaminophenyl)ethyl]-9-cyano-1,3,4,4a,5, 10b-hexahydro-2H-chromeno[3,4-b]pyridine Hydrochloride The expected product is obtained in accordance with the process described in Example 4, using as starting material 9-cyano-1,3,4,4a,5,10hexahydro-2H-chromeno-[3,4-c] pyridine (the latter having been prepared from the analogue hydroxylated in the 9 position described in J. Med. Chem., 1989, 32, 720).

EXAMPLE 55

(4aα,10bβ)-9-Cyano-4-furylmethyl-1,3,4,4a,5,10b-hexahydro-2H-chromeno[3,4-b]pyridine Hydrochloride The expected product is obtained in accordance with the process described in Example 27, using as starting material 9-cyano-1,3,4,4a,5,10b-hexahydro-2H-chromeno[3,4-c] pyridine (the latter having been prepared from the analogue hydroxylated in the 9 position described in J. Med. Chem., 1989, 32, 720).

EXAMPLE 56

4-Bromo-N-[4-((4aα,10bβ)-9-cyano-1,3,4,4a,5,10b-hexahydro-2H-chromeno[3,4-b]pyrid-4-yl) butyl]benzamide Hydrochloride The expected product is obtained in accordance with the process described in Example 15, using as starting material 9-cyano-1,3,4,4a,5,10b-hexahydro-2H-chromeno[3,4-c] pyridine (the latter having been prepared from the analogue hydroxylated in the 9 position described in J. Med. Chem., 1989, 32, 720).

EXAMPLE 57

4-Cyano-N-[4-((4aα,10bβ)-9-cyano-1,3,4,4a,5,10b-hexahydro-2H-chromeno[3,4-b]pyrid-4-yl)butyl] benzamide Hydrochloride The expected product is obtained in accordance with the process described in Example 13, using as starting material 9-cyano-1,3,4,4a,5,10b-hexahydro-2H-chromeno[3,4-c] pyridine (the latter having been prepared from the analogue hydroxylated in the 9 position described in J. Med. Chem., 1989, 32, 720).

EXAMPLE 58

N-[4-((4aα,10bβ)-9-Cyano-1,3,4,4a,5,10b-hexahydro-2H-chromeno3,4-b]pyrid-4-yl)butyl]-4-phenylbenzamide Hydrochloride The expected product is obtained in accordance with the process described in Example 14, using as starting material 9-cyano-1,3,4,4a,5,10b-hexahydro-2H-chromeno[3,4-c] pyridine (the latter having been prepared from the analogue hydroxylated in the 9 position described in J. Med. Chem., 1989, 32, 720).

EXAMPLE 59

4-Bromo-N-[4-((4aα,10bβ)-9-cyano-1,3,4,4a,5,10b-hexahydro-2H-chromeno[3,4-b]pyrid-4-yl)butyl] benzenesulphonamide Hydrochloride The expected product is obtained in accordance with the process described in Example 35, using as starting material 9-cyano-1,3,4,4a,5,10b-hexahydro-2H-chromeno[3,4-c] pyridine (the latter having been prepared from the analogue hydroxylated in the 9 position described in J. Med. Chem., 1989, 32, 720).

EXAMPLE 60

In Vitro Measurement of the Affinity to $D_2$ and $D_3$ Receptors

The affinity of the compounds of the invention to $D_2$ and $D_3$ receptors (expressed independently and in a stable manner in CHO cells) was determined with membrane preparations using [$^{125}$I]-iodosulpiride as radioligand (Sokoloff et aL, quoted reference). The results are expressed as pKi.

The results demonstrate in vitro the selectivity of the compounds of the invention for $D_3$ receptors compared with $D_2$ receptors. This is true especially of the compound of Example 4, for which the selectivity is greater than log 1.5.

EXAMPLE 61

In Vivo Demonstration of the Selectivity for $D_3$ Receptors Compared with $D_2$ Receptors The in vivo selectivity of the compounds of the invention for $D_3$ receptors compared with $D_2$ receptors was demonstrated in the rat by the capacity of the compounds to modulate the hypothermia induced by the $D_3$ dopaminergic agonist 7-OH-DPAT, control of the body temperature being dependent on the post-synaptic $D_3$ receptor (M. Millan, quoted reference).

Method

The tests were carried out on male Wistar rats weighing 200–250 g placed in individual cages with free access to food and water. The products were dissolved in distilled water to which several drops of lactic acid are added. The injections were carried out by the subcutaneous route.

In a first period the test product or the carrier is injected, then the rats are put back in their cages for 30 minutes. In a second period the rats are given an injection of 7-OH-DPAT or carrier and are placed back in their cages. Thirty minutes later, the rectal temperature is measured (using a digital thermistoprobe, Millan et al., J. Pharmacol. Exp. Ther., 1993, 264, 1364–76), and the difference in relation to base values is determined ($\Delta T° C.$).

Results

The compounds of the invention appear to be capable of significant modulation of the hypothermia induced by 7-OH-DPAT (in the case of the more active compounds, the effect of the reference $D_3$ ligand is virtually nullified).

EXAMPLE 62

Pharmaceutical Composition

Formulation for the preparation of 1000 tablets each containing 10 mg of active ingredient

| | |
|---|---|
| compound of Example 4 | 10 g |
| hydroxypropyl cellulose | 2 g |
| wheat starch | 10 g |
| lactose | 100 g |
| magnesium stearate | 3 g |
| talc | 3 g |

We claim:
1. A compound selected from those of formula (I):

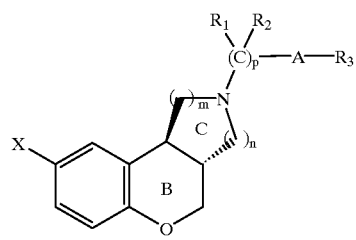

(I)

wherein:

m is 3, n is 0, p is 1 to 6 inclusive, the junction between the B and C rings is in the trans configuration, X represents cyano or —CO—NR$_4$R$_5$, R$_4$ and R$_5$ being selected hydrogen, linear or branched (C$_1$–C$_6$)-alkyl, (C$_3$–C$_7$)-cycloalkyl, and optionally substituted aryl, A represents a σ bond or a group selected from —NR—CO—, —CO—NR—, NR—SO$_2$ and SO$_2$—NR wherein R represents hydrogen or linear or branched (C$_1$–C$_6$)-alkyl, R$_1$ and R$_2$ each independently represent hydrogen or linear or branched (C$_1$–C$_6$)-alkyl, R$_3$ represents:
hydrogen, or phenyl, naphthyl or heteroaryl each of which is optionally substituted by one or more halogen, linear or branched (C$_1$–C$_6$)-alkyl, linear or branched (C$_1$–C$_6$)-alkoxy, hydroxy, cyano, amino, nitro, carboxy, linear or branched (C$_1$–C$_6$)-perhaloalkyl, sulpho, acylamino, linear or branched (C$_1$–C$_6$)-alkylsulphonyl or linear or branched (C$_1$–C$_6$)-alkylsulphonylamino, 2-indolinon-5-yl, or aryloxy or arylthio (with the proviso that in that case A represents σ bond), their enantiomers, diastereoisomers, and addition salts thereof with a pharmaceutically-acceptable acid or base.

2. Compounds of claim 1 wherein X represents cyano, their enantiomers, diastereoisomers, and addition salts thereof with a pharmaceutically-acceptable acid or base.

3. Compounds of claim 1 wherein A represents a σ bond, their enantiomers, diastereoisomers, and addition salts thereof with a pharmaceutically-acceptable acid or base.

4. Compounds of claim 1 wherein A represents —NR—CO— or NR—SO$_2$, their enantiomers, diastereoisomers, and addition salts thereof with a pharmaceutically-acceptable acid or base.

5. Compounds of claim 1 wherein R$_3$ represents optionally substituted phenyl, their enantiomers, diastereoisomers, and addition salts thereof with a pharmaceutically-acceptable acid or base.

6. A compound selected from the group consisting of (4aα,10bβ)-9-cyano-4-propyl-1,3,4,4a,5,10b-hexahydro-2H-chromeno[3,4-b]pyridine and a pharmaceutically-acceptable acid addition salt thereof.

7. A compound of claim 6 which is (4aα,10bβ)-9-cyano-4-propyl-1,3,4,4a,5,10b-hexahydro-2H-chromeno[3,4-b]pyridine hydrochlo-ride.

8. A pharmaceutical composition useful as a $D_3$ receptor ligand comprising as active principle an effective amount of a compound as claimed in claim 1, together with one or more pharmaceutically-acceptable excipients or vehicles.

9. A method for treating a living body afflicted with a condition selected from depression, schizophrenia, psychoses Parkinson's disease, memory disorders, and disorders associated with drug abuse, comprising the step of administering to the living body an amount of a compound of claim 1 which is effective for alleviation of said condition.

* * * * *

UNITED STATES PATENT AND TRADEMARK OFFICE
CERTIFICATE OF CORRECTION

PATENT NO.    : 6,326,377 B1
DATED         : December 4, 2001
INVENTOR(S)   : Gilbert Lavielle et al.

It is certified that error appears in the above-identified patent and that said Letters Patent is hereby corrected as shown below:

<u>Column 28,</u>
Line 10, -- selected hydrogen -- should read "selected from hydrogen".

Signed and Sealed this

Nineteenth Day of March, 2002

Attest:

JAMES E. ROGAN
*Director of the United States Patent and Trademark Office*

*Attesting Officer*